(12) United States Patent
Sakiyama

(10) Patent No.: US 7,048,685 B2
(45) Date of Patent: May 23, 2006

(54) MEASURING ENDOSCOPE SYSTEM

(75) Inventor: Katsunori Sakiyama, Akiruno (JP)

(73) Assignee: Olympus Corporation (JP)

( * ) Notice: Subject to any disclaimer, the term of this patent is extended or adjusted under 35 U.S.C. 154(b) by 514 days.

(21) Appl. No.: 10/209,219

(22) Filed: Jul. 29, 2002

(65) Prior Publication Data

US 2004/0019255 A1    Jan. 29, 2004

(51) Int. Cl.
*A61B 1/04* (2006.01)
(52) U.S. Cl. .................. 600/175; 600/166; 348/75
(58) Field of Classification Search ............... 600/101, 600/103, 109, 175, 111, 166, 176, 118; 348/65, 348/72, 74, 75
See application file for complete search history.

(56) References Cited

U.S. PATENT DOCUMENTS

| 5,408,996 A | * | 4/1995 | Salb ........................... 600/317 |
| 5,860,912 A | * | 1/1999 | Chiba .......................... 600/111 |
| 6,063,023 A | * | 5/2000 | Sakiyama et al. .......... 600/118 |
| 2001/0022860 A1 | * | 9/2001 | Kitamura et al. ........... 382/284 |
| 2002/0161284 A1 | * | 10/2002 | Tanaka ....................... 600/176 |

FOREIGN PATENT DOCUMENTS

| JP | 60-237419 | 11/1985 |
| JP | 10-248806 | 9/1998 |

* cited by examiner

*Primary Examiner*—John P. Leubecker
(74) *Attorney, Agent, or Firm*—Ostrolenk, Faber, Gerb & Soffen, LLP

(57) ABSTRACT

A measuring endoscope system includes a menu display module that selects a menu according to display data which is associated in advance with any of a plurality of optical adaptors, and a measuring program for performing measurement according to the result of the selection performed by the menu display module. Consequently, in the measuring endoscope system, when a user designates an optical adaptor using an optical adaptor selection screen image displayed on an LCD by the menu display module, a measuring technique associated with the optical adaptor is automatically selected. When a user wants to perform measurement using the measuring endoscope system, the user should merely press a measurement execution switch included in an endoscopic operation unit. Thus, measurement in which the selected measuring technique is implemented is carried out. Consequently, the present invention has succeeded in improving the maneuverability of a measuring endoscope system in measurement and improving the efficiency thereof in inspection.

16 Claims, 8 Drawing Sheets

MEASURING ENDOSCOPE SYSTEM

This application claims the benefit of Japanese Application No. 2000-101122 filed in Japan on Apr. 3, 2000, the contents of which are incorporated by reference.

BACKGROUND OF THE INVENTION

1. Field of the Invention

The present invention relates to a measuring endoscope system that images an object to be inspected (object) and then measures the object to be inspected.

2. Description of the Related Art

In general, it is necessary to measure an object to be inspected (object) for the purpose of inspecting the detail of the object to be inspected (object).

When it comes to conventional endoscope systems, a measuring means that enables measurement of an object to be inspected (object) is needed for realization of endoscopic observation.

In order to meet the diverse demands, various proposals have been made of the measuring means for endoscopes, and disclosed in, for example, Japanese Unexamined Patent Application Publications Nos. 10-248806 and 60-237419 filed previously by the present applicant.

The former (Japanese Unexamined Patent Application Publication No. 10-248806) has disclosed a measuring endoscope system enabling stereoscopic (hereinafter stereo) measurement.

The latter (Japanese Unexamined Patent Application Publication No. 60-237419) has disclosed a length measuring optical adaptor for endoscopes that permits implementation of a comparison measurement technique. The comparison measurement technique is such that an index mark is projected on an object surface that is an object to be inspected (object), and compares an entity with the projected index mark for the purpose of measurement.

The measuring endoscope system described in the former Japanese Unexamined Patent Application Publication No. 10-248806 has an optical adaptor, which includes two optical systems needed to image an object to be inspected for the purpose of measurement, freely detachably attached to an endoscope body. The measuring endoscope system converges images, which are formed by two systems of lenses included in the optical adaptor, on one imaging device, processes at least the produced endoscopic image data, and performs measurement.

The measuring endoscope system includes a measuring means that performs reading, correction, coordinate transformation, and calculation. Specifically, the measuring means reads information from a recording medium on which optical data items concerning optical adaptors are recorded. Moreover, the measuring means corrects optical data according to an error in the position of an imaging module included in the endoscope body. Moreover, the measuring means performs coordinate transformation on images of an object to be measured according to the corrected optical data. Furthermore, the measuring means calculates coordinates, which represent any point in the three-dimensional space, by matching the images, which have been subjected to the coordinate transformation, with each other.

In the above measuring endoscope system, two images of an object to be inspected (object) picked up by the imaging device via the optical adaptor are subjected to coordinate transformation, and the resultant two images are matched with each other using the resultant image data items. Thus, coordinates representing any point on the object to be inspected in the three-dimensional space are calculated. Consequently, the present invention has succeeded in realizing a measuring endoscope system that is inexpensive and offers high precision in measurement.

Moreover, the measuring endoscope system is designed primarily for stereoscopic (stereo) measurement. For normal measurement, a normal optical adaptor including one optical system is detachably attached to the tip of an endoscope. An image formed by the normal optical adaptor can be used to perform normal measurement.

On the other hand, the length measuring optical adaptor for endoscopes described in the latter Japanese Unexamined Patent Application Publication No. 60-237419 is an optical adaptor that is freely detachably attached to the tip of an endoscope body and that has an index mark and a projection optical system which projects the index mark. Thus, the length measuring optical adaptor is realized as a low-cost length measuring optical adaptor. When the length measuring optical adaptor for endoscopes is attached to the endoscope body, a length measuring endoscope (measuring endoscope) is realized. Moreover, length measuring endoscopes producing different images or offering a field of view in different directions can be realized at low cost.

However, the measuring endoscope system described in the Japanese Unexamined Patent Application Publication No. 10-248806 and the length measuring optical adaptor for endoscopes described in the Japanese Unexamined Patent Application Publication No. 60-237419 have drawbacks described below.

For example, in a certain conventional measuring endoscope system, two types of optical adaptors, that is, a stereo measurement optical adaptor and a normal optical adaptor can be detachably attached to an endoscopic distal part. When the measuring endoscope system is designed to be able to perform both stereo measurement and normal measurement, a measuring program conventionally includes two routines, for example, a module for displaying an optical adaptor selection menu and prompting a user to select any of optical adaptors and a module for selecting and implementing a measuring technique optimal to the selected optical adaptor. The two modules are run independently of each other.

In other words, as far as the conventional measuring endoscope system is concerned, the optical adaptor selection menu and a measuring technique switching menu are independent of each other. Therefore, when an object to be inspected is measured, a measuring technique not associated with a selected optical adaptor maybe designated. For this reason, there is a fear that the conventional measuring endoscope system may have the performance thereof deteriorated.

Moreover, the conventional measuring endoscope system displays a menu for prompting a user to switch measuring techniques, and thus permit a user to select and implement a measuring technique. Therefore, the conventional measuring endoscope has a drawback that handling a user have to perform for measurement is so complex as to annoy the user.

OBJECTS AND SUMMARY OF THE INVENTION

An object of the present invention is to provide a measuring endoscope system capable of preventing implementation of a measuring technique not associated with an optical adaptor, and performing a measurement associated with an optical adaptor through simple handling. Thus, the present invention attempts to improve the maneuverability of a measuring endoscope system in measurement and the efficiency thereof in inspection.

Another object of the present invention is to provide an inexpensive measuring endoscope system capable of offering high precision in measurement.

Still another object of the present invention is to provide a measuring endoscope system capable of reliably imaging the outline of a mask mounted on an optical adaptor without deterioration of precision in measurement.

Yet another object of the present invention is to provide a measuring endoscope system that is devoid of the fear that a measuring technique which mismatches with an optical adaptor may be implemented, and that reliably and correctly measures an object to be inspected.

According to the present invention, a measuring endoscope system that processes an object image produced by imaging an object to be inspected and measures the object to be inspected consists mainly of:

a plurality of types of optical adaptors each of which is detachably attached to an endoscopic distal part and converges an object image on an imaging device incorporated in the endoscopic distal part;

a menu display module that selects a selection menu according to display data associated in advance with any of the plurality of optical adaptors; and a measuring means that performs measurement according to the results of selection performed by the menu display module.

Other features of the present invention and advantages thereof will be fully apparent from the description below.

DETAILED DESCRIPTION OF THE PREFERRED EMBODIMENTS

Figure 1:
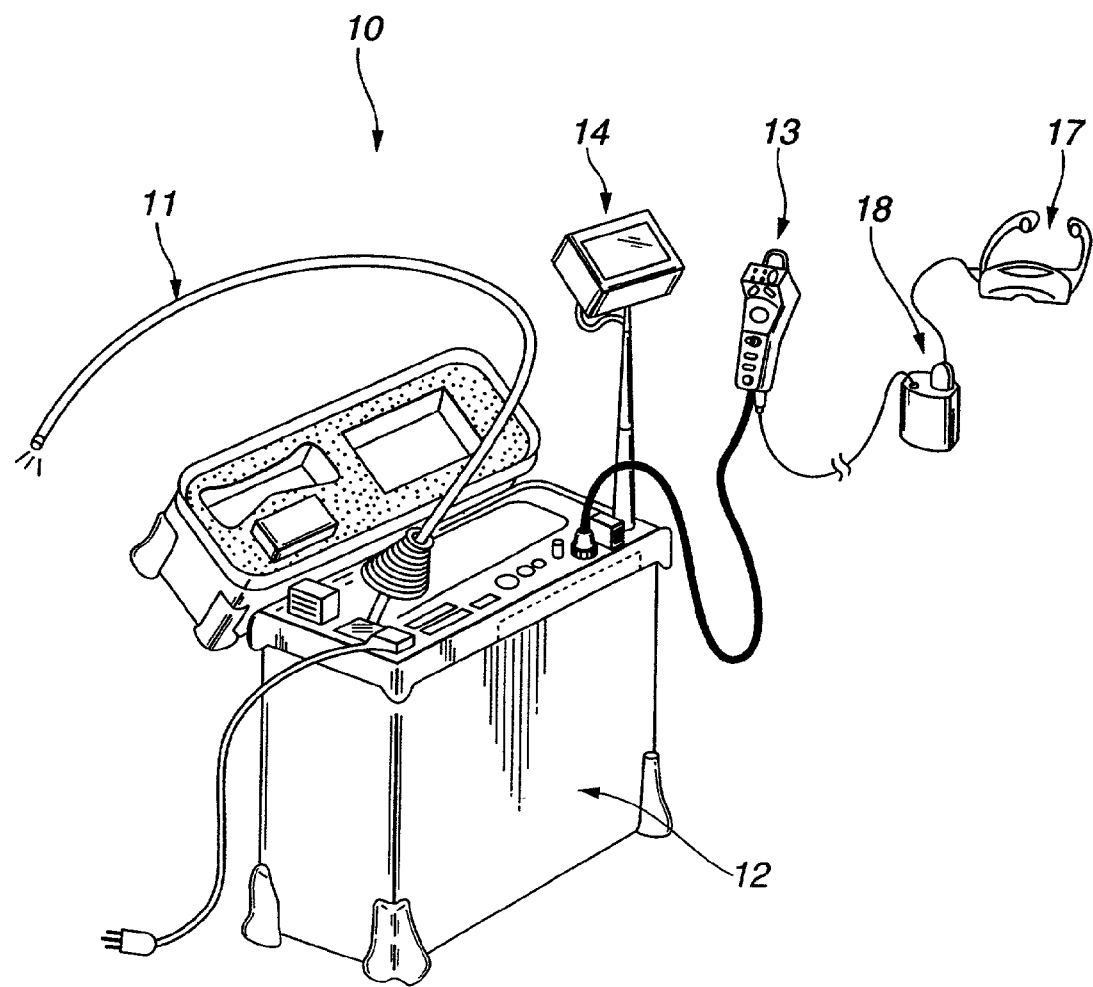
FIG. 1 is a perspective view showing the configuration of a measuring endoscope system in accordance with an embodiment of the present invention.

Referring to the drawings, embodiments of the present invention will be described below.

(First Embodiment)

Figure 2:
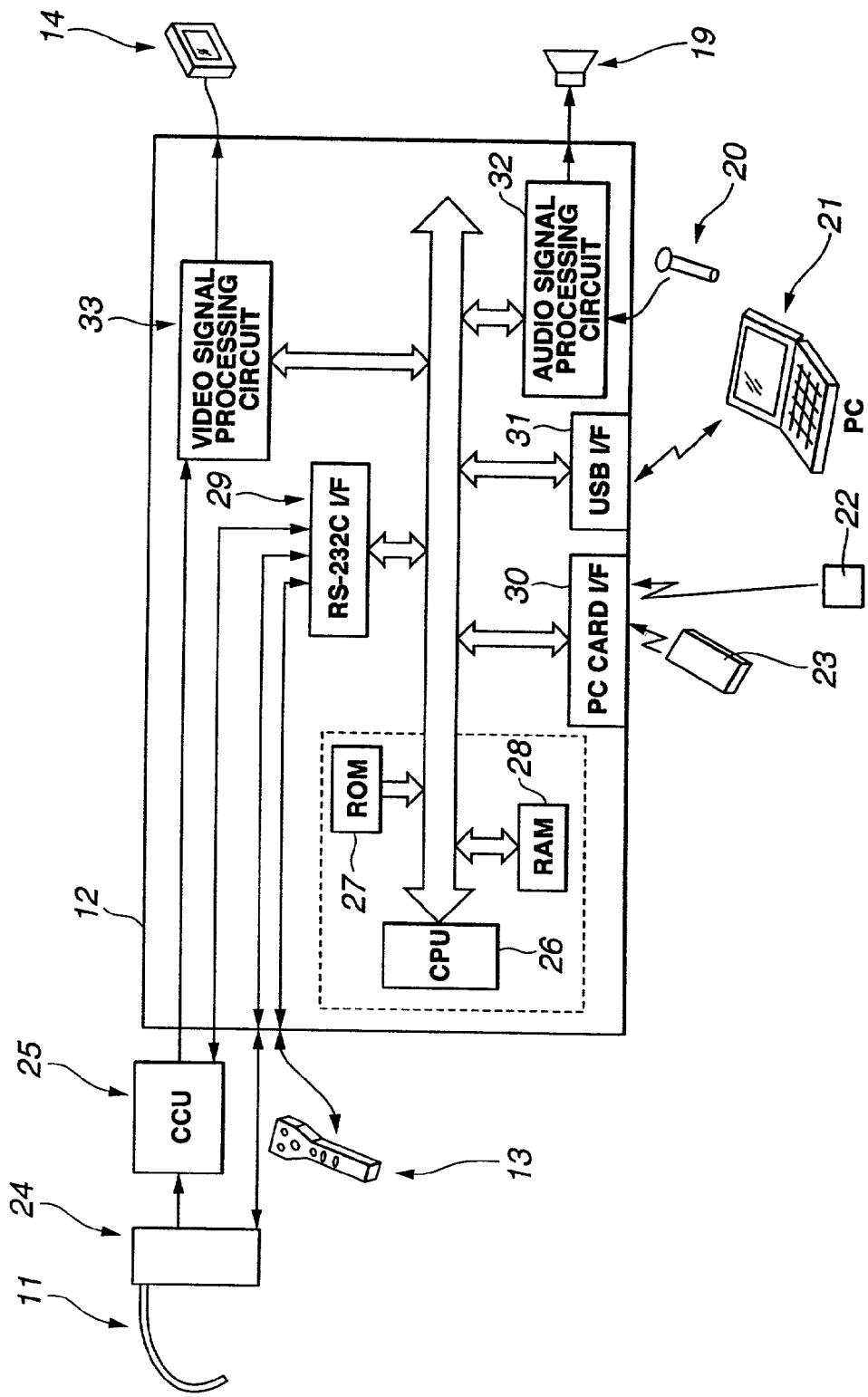
FIG. 2 is a block diagram showing the electrical circuitry of the measuring endoscope system shown in FIG. 1.
Figure 3:
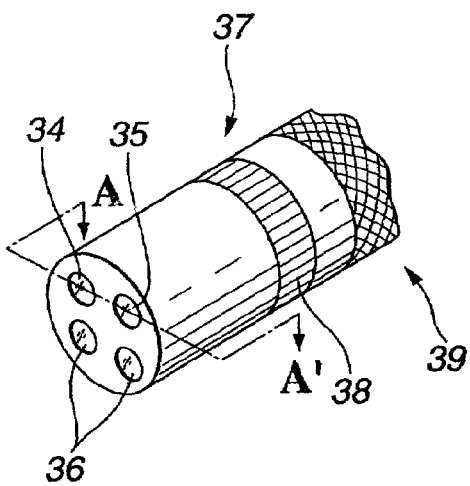
FIG. 3 is a perspective view showing the appearance of an endoscopic distal part having a stereo measurement adaptor attached thereto.
Figure 4:
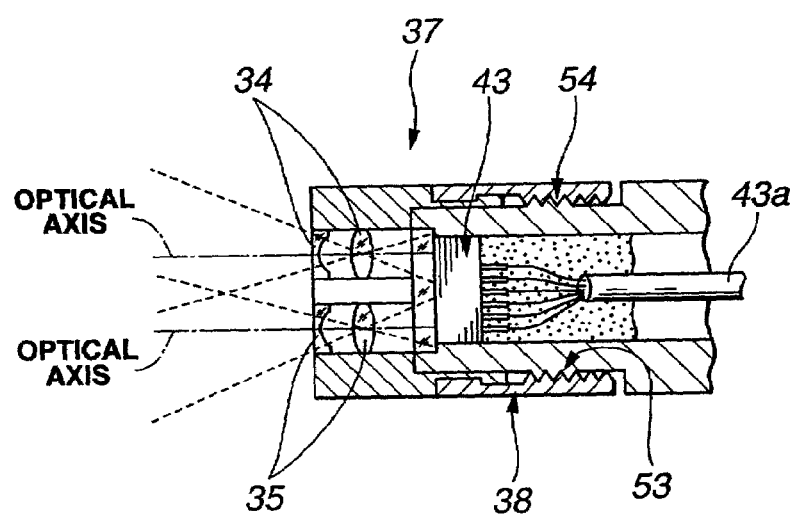
FIG. 4 is an A—A sectional view of the endoscopic distal part shown in FIG. 3.
Figure 5:
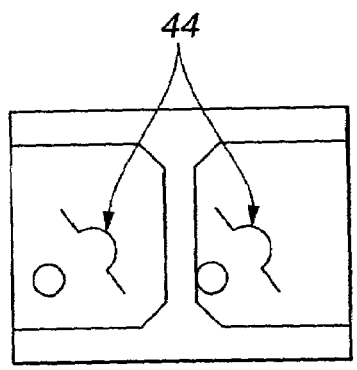
FIG. 5 shows an endoscopic image produced by the endoscope system having the stereo measurement adaptor.
Figure 6:
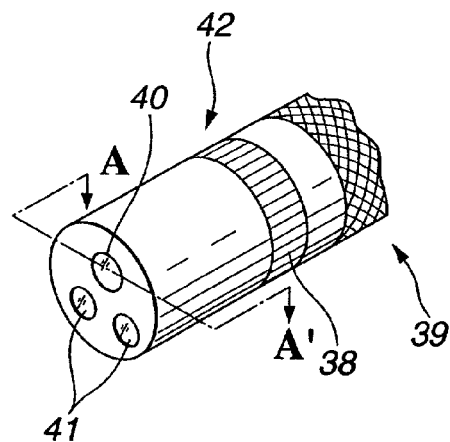
FIG. 6 is a perspective view showing the appearance of the endoscopic distal part having a normal optical adaptor attached thereto.
Figure 7:
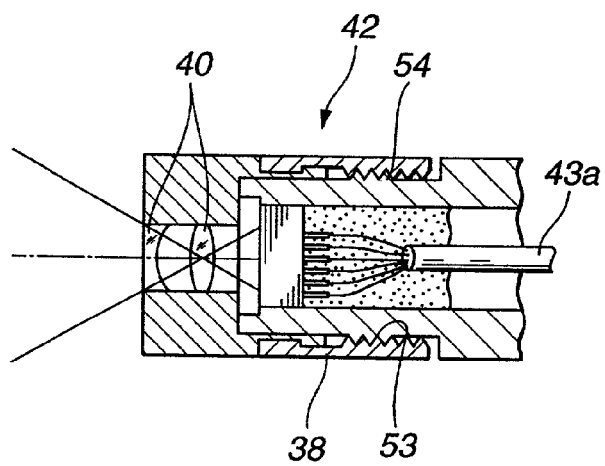
FIG. 7 is an A—A sectional view of the endoscopic distal part shown in FIG. 6.
Figure 8:
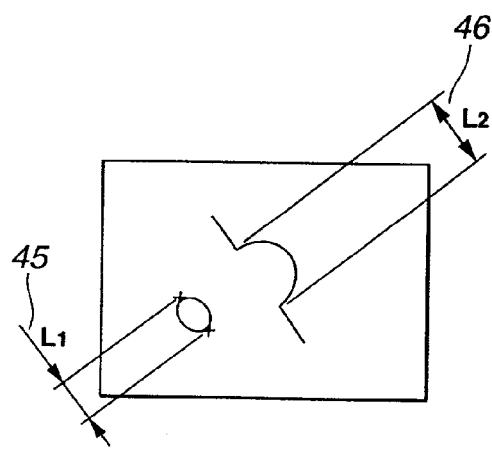
FIG. 8 shows an endoscopic image produced by the endoscope system having the normal optical adaptor.
Figure 9A:
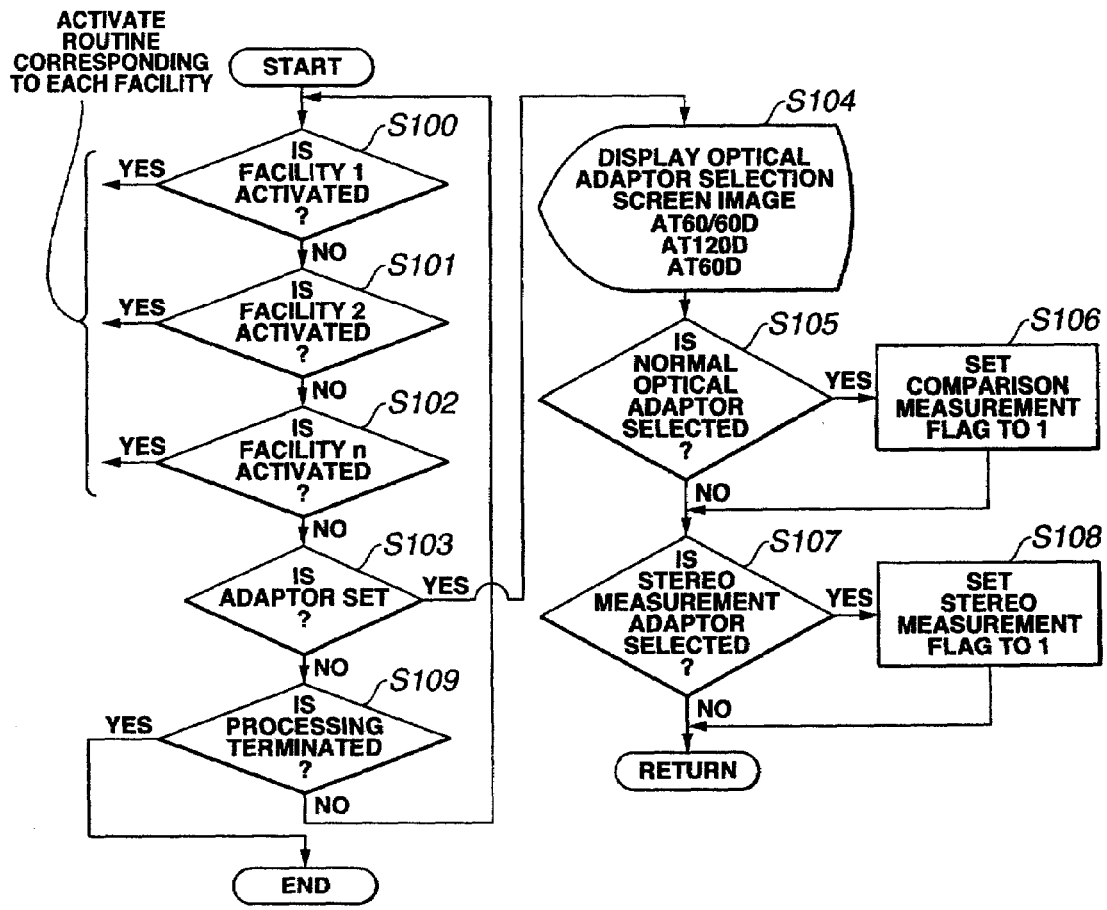
FIG. 9A is a main flowchart describing an example of control actions performed by a CPU and characterizing the present embodiment.
Figure 9B:
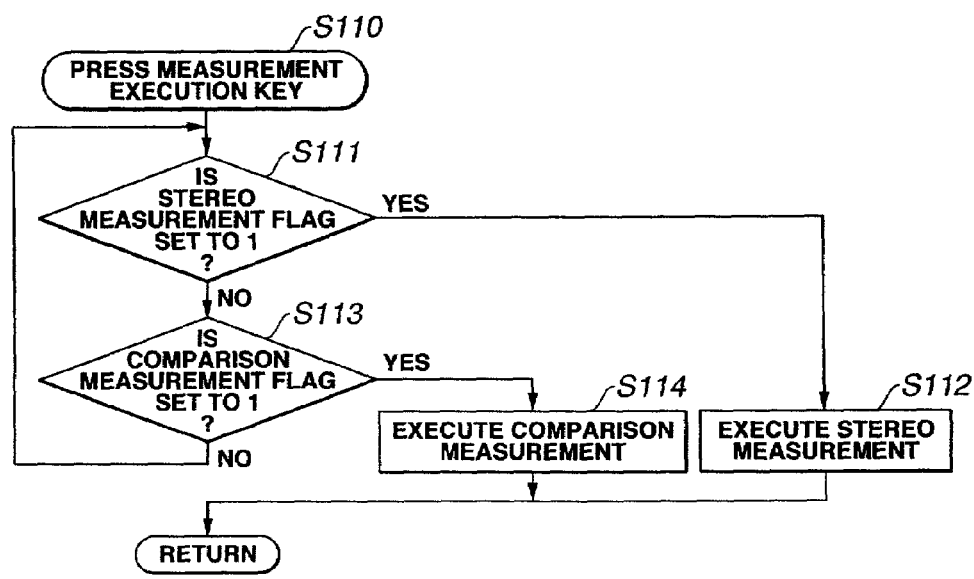
FIG. 9B is a flowchart describing a measurement <executing routine assigned to facility 1 described in the main flowchart of FIG. 9A.
Figure 10:
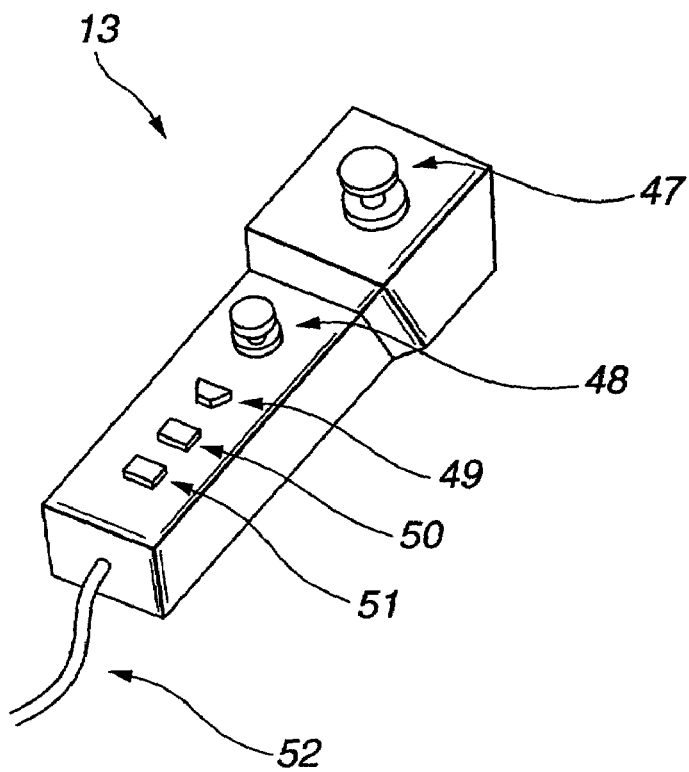
FIG. 10 is a perspective view showing the appearance of a remote controller.
Figure 11:
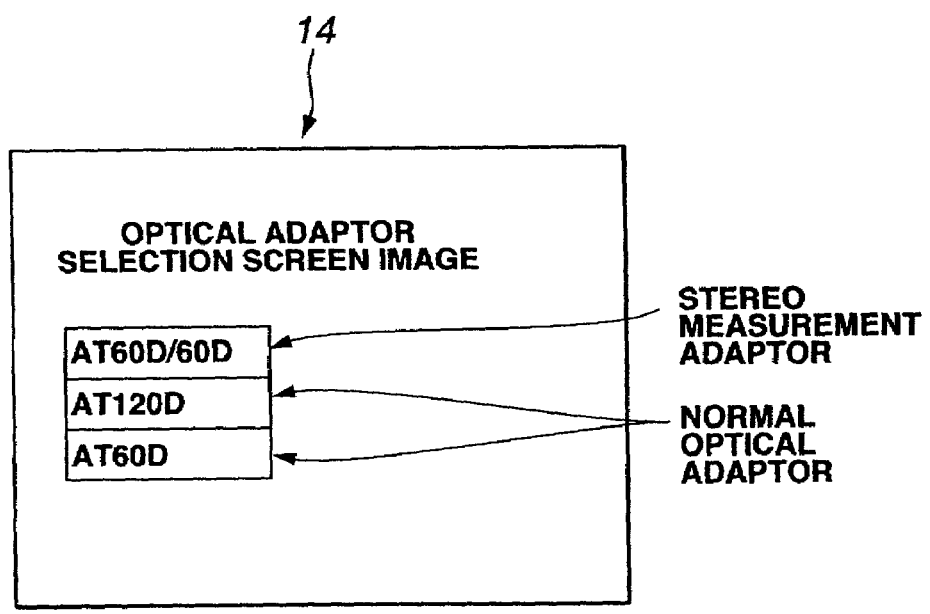
FIG. 11 shows an example of an optical adaptor selection screen image displayed on an LCD.
Figure 12:
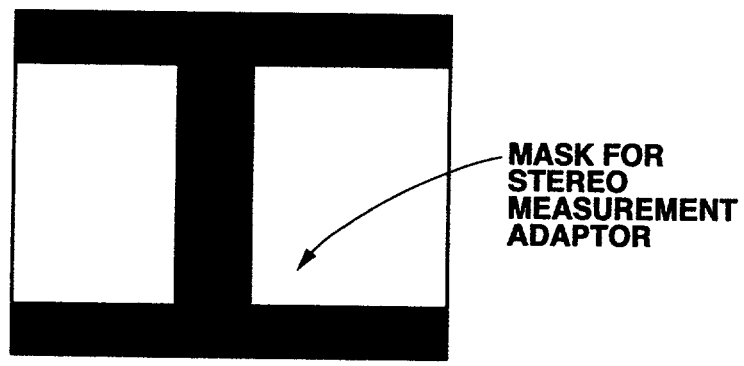
FIG. 12 shows an image rendering the outline of a mask mounted on a stereo measurement adaptor.
Figure 13:
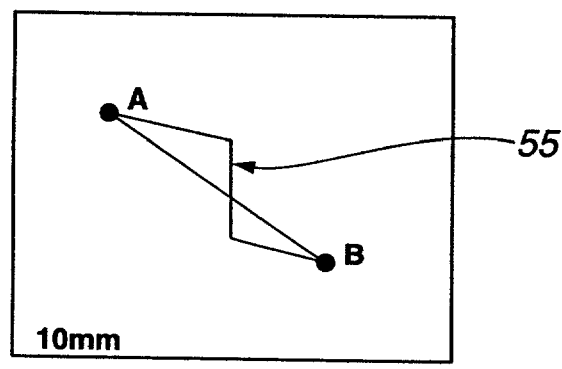
FIG. 13 shows an example of a point-to-point length measurement image.
Figure 14:
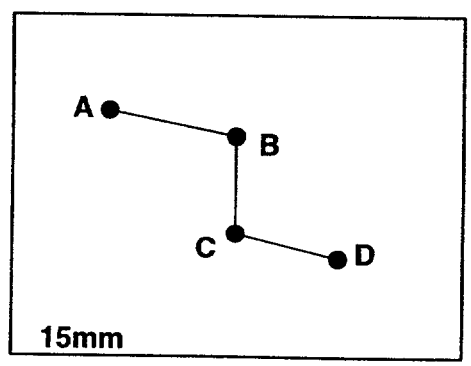
FIG. 14 shows an example of an image in which a sum total of lengths is calculated.
Figure 15:
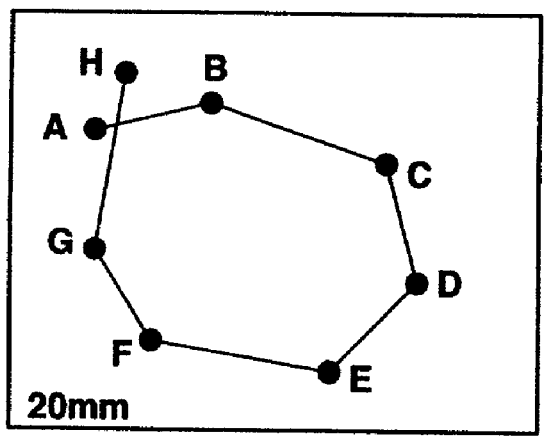
FIG. 15 shows an example of an image rendering a plurality of points that is sequentially traced in order to draw segments for the purpose of calculating an area.
Figure 16:
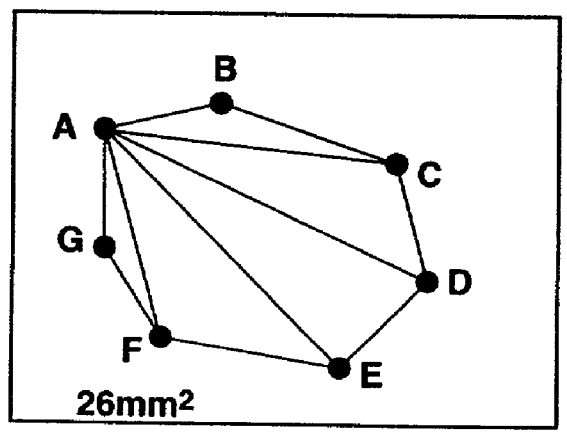
FIG. 16 shows an example of an image in which a graphic defined with segments is closed by running a measuring program with the image shown in FIG. 15 displayed.

FIG. 1 to FIG. 16 show a first embodiment of a measuring endoscope system in accordance with the present invention. FIG. 1 is a perspective view showing the configuration of a measuring endoscope system in accordance with the first embodiment of the present invention. FIG. 2 is a block diagram showing the electrical circuitry of the measuring endoscope system shown in FIG. 1. FIG. 3 is a perspective view showing the appearance of an endoscopic distal part having a stereo measurement adaptor attached thereto. FIG. 4 is an A—A sectional view of the endoscopic distal part shown in FIG. 3. FIG. 5 shows an endoscopic image produced by the endoscope system with the stereo measurement adaptor. FIG. 6 is a perspective view showing the appearance of an endoscopic distal part having a normal optical adaptor attached thereto. FIG. 7 is an A—A sectional view of the endoscopic distal part shown in FIG. 6. FIG. 8 shows an endoscopic image produced by the endoscope system with the normal optical adaptor. FIG. 9A is a main flowchart describing an example of control actions that are performed by a CPU and characterize the measuring endoscope system. FIG. 9B is a flowchart describing a measurement executing routine to be assigned to facility 1 described in the main flowchart of FIG. 9A. FIG. 10 is a perspective view showing the appearance of a remote controller. FIG. 11 shows an example of an optical adaptor selection screen image displayed on an LCD. FIG. 12 shows an image rendering the outline of a mask mounted on a stereo measurement adaptor. FIG. 13 shows an example of a point-to-point length measurement image. FIG. 14 shows an example of an image in which a sum total of lengths is calculated. FIG. 15 shows an example of an image in which a plurality of points is sequentially traced to draw segments for the purpose of calculation of an area. FIG. 16 shows an example of an image in which a graphic defined with segments is closed by running a measuring program with the image shown in FIG. 15 displayed.

The configuration of a measuring endoscope system 10 in accordance with the present embodiment will be described below.

As shown in FIG. 1, the measuring endoscope system 10 consists mainly of an endoscopic insertion unit 11, a control unit 12, a remote controller 13, a liquid crystal monitor (hereinafter LCD) 14, a face-mounted display (hereinafter FMD) 17, and a FMD adaptor 18. At least two types of optical adaptors for stereo measurement and normal measurement are freely detachably attached to the endoscopic insertion unit 11. The endoscopic insertion unit 11 is stored in the control unit 12. The remote controller is handled in order to control various actions to be performed in the whole system. An endoscopic image or the contents of control (for example, a selection menu) are displayed on the LCD 14.

The FMD 17 permits a user to see a normal endoscopic image or to quasi-stereoscopically see the endoscopic image as a stereoscopic (stereo) image. The FMD adaptor 18 transmits image data to the FMD 17.

Referring to FIG. 2, the configuration of the endoscope system will be described below.

As shown in FIG. 2, the endoscopic insertion unit 11 is connected to an endoscope unit 24. The endoscope unit 24 is, for example, as shown in FIG. 1, incorporated in the control unit 12. The endoscopic unit 24 consists mainly of a light source unit that provides illumination light needed for imaging and that is not shown, and an electric angling unit that electrically freely angles the endoscopic insertion unit 11.

The endoscopic insertion unit 11 has a solid-state imaging device 43 (see FIG. 4) incorporated in the distal part thereof. An image signal produced by the solid-state imaging device 43 is transferred to a camera control unit (hereinafter CCU) 25. The CCU 25 converts a received image signal into a video signal conformable to the NTSC standard or the like, and transmits the video signal to major groups of processing circuits incorporated in the control unit 12.

The control unit 12 has, for example, as shown in FIG. 2, the major groups of circuits incorporated therein. As shown in FIG. 2, the major groups of circuits include a CPU 26, a ROM 27, a RAM 28, a PC card interface 30, a USB interface 31, an RS-232C interface 29, an audio signal processing circuit 32, and a video signal processing circuit 33. The CPU 26 extends control so as to activate various facilities according to a main program.

The RS-232C interface 29 permits connections of the control unit 12 to the CCU 25, endoscope unit 24, and remote controller 13 respectively. Through the RS-232C interface 29, the control unit 12 controls the CCU 25 and endoscope unit 24, and communicates with the CCU 25 and endoscope unit 24 so as to control their actions according to handling of the remote controller 13 that is used to instruct an action.

The USB interface 31 is an interface through which the control unit 12 is electrically connected to a personal computer 21. When the control unit 12 is connected to the personal computer 21 through the USB interface 21, the personal computer 21 can give various instructions to the control unit 12 so as to instruct display of an endoscopic image or to instruct image processing for measurement. Moreover, control information and data needed to achieve various tasks can be transferred between the control unit 12 and personal computer 21.

A PCMCIA memory card 22 or a compact flash memory card 23 that is a memory card serving as a recording medium can be inserted in the PC card interface 30 so that it can be removed freely.

When the memory card is inserted in the PC card interface 30, control data or image data stored on the memory card can be fetched into the control unit 12 through the PC card interface 30, and reproduced. Moreover, control data, image data, or any other data can be recorded on the memory card through the PC card interface 30.

The video signal processing circuit 33 synthesizes a video signal sent from the CCU 25 with a display signal that represents a selection menu and that is produced under the control of the CPU 26. This enables display of the synthetic image produced by synthesizing an endoscopic image sent from the CCU 25 and the selection menu that is a graphic. Furthermore, the video signal processing circuit 33 processes the synthetic signal so that the synthetic image can be displayed on the screen of the LCD 14, and transfers the resultant signal to the LCD 14. Consequently, the synthetic image of the endoscopic image and selection menu is displayed on the LCD 14.

Incidentally, the video signal processing circuit 33 can process a signal so that an endoscopic image or a selection menu can be displayed solely.

The audio signal processing circuit 32 receives an audio signal that is recorded on a recording medium such as a memory card according to sounds collected by a microphone 20, or an audio signal that is produced by reproducing sounds from the recording medium such as memory card. The audio signal processing circuit 32 performs required processing (amplification or the like) on the audio signal so as to reproduce sounds, and delivers the sounds through a loudspeaker 19. Consequently, the control unit 12 radiates the sounds reproduced according to the audio signal through the speaker 19.

The CPU 26 runs a program stored in the ROM 27, controls various groups of circuits so as to control actions to be performed in the entire system. Thus, processing is performed based on a purpose of use.

Next, a description will be made of the configuration of the remote controller 13 and an example of how the CPU 26 controls programmed actions depending on the handling of the remote controller 13.

The remote controller 13 employed in the measuring endoscope system 10 of the present embodiment has been innovated in order to improve the maneuverability thereof in measurement or the like.

The remote controller 13 has, as shown in FIG. 10, at least a joystick 47, a lever switch 48, a Freeze switch 49, a Store switch 50, and a measurement execution switch 51 disposed on the top thereof. Specifically, the remote controller 13 has the switches arranged so that a user can handle them easily.

The joystick 47 of the remote controller 13 is a switch used to angle the endoscopic distal part. The joystick 47 can give an instruction to angle the endoscopic distal part in any direction of 360°. Moreover, the lever switch 48 is a switch used to move a pointer when a menu item is selected from any of various menus that are graphically displayed or when measurement is performed. The lever switch 48 has substantially the same shape as the joystick 47.

The Freeze switch 49 is used to display an image frame, which is included in an endoscopic motion picture displayed on the LCD 14, as a still image. When the Freeze switch 49 has been pressed in order to display a still image, the Store switch 50 is used to record the still image on the PCMCIA memory card 22 (see FIG. 2). The measurement execution switch 51 is used to run measuring software.

The Freeze switch 49, Store switch 50, and measurement execution switch 51 are formed with, for example, pushbutton switches that are pressed to be turned on or off. Moreover, any facility other than the foregoing facility to move a pointer may be assigned to the lever switch 48.

For example, zooming-in and zooming-out facilities may be assigned to the lever switch 48 so that: when the lever switch 48 is turned right, an image will be zoomed in; and when the lever switch 48 is turned left, an image will be zoomed out.

Moreover, normally, when a zoomed image is used to measure an object to be inspected (object), the measurement cannot be achieved correctly because the magnification of the zoomed image is different from the original one.

In this case, the measurement execution switch 51 of the remote controller 13 is utilized. Specifically, when the measurement execution switch 51 is pressed, the CPU 26 receives a measurement signal produced responsively to the press of the measurement execution switch 51. The CPU 26 relieves the zooming facility immediately and extends control so that an image will be frozen for measurement. Alternatively, the remote controller 13 may extend control so that the CPU 26 can perform measurement using the zoomed image in consideration of the magnification for zooming.

Next, the configuration of a stereo measurement adaptor to be employed in the measuring endoscope system 10 of the present embodiment will be described with reference to FIG. 3 to FIG. 5.

FIG. 3 and FIG. 4 show the endoscopic distal part 39 having a stereo measurement adaptor 37 attached thereto. The stereo measurement adaptor 37 is secured by meshing a female screw 53 threaded on a locking ring 38 with a male screw 54 threaded on the endoscopic distal part 39.

Moreover, the stereo measurement adaptor 37 has a pair of illumination lenses 36 and two objective lenses 34 and 35 contained in the distal face thereof. The two objectives 34 and 35 converge two images on the imaging device 43 disposed in the endoscopic distal part 39. An image signal produced by the imaging device 43 is transferred to the CCU 25 via the endoscope unit 24 over a signal line 43a electrically coupled to the imaging device. The CCU 25 converts the received image signal into a video signal, and then transfers the video signal to the video signal processing circuit 33. Consequently, an image like the one shown in FIG. 5 is displayed on the LCD 14.

When the measuring endoscope system 10 of the present embodiment performs stereo measurement, an endoscopic image shown in FIG. 5 is used to stereoscopically measure an object to be measured on the basis of optical data read from a recording medium (for example, a compact flash memory card) on which optical data concerning, for example, the stereo measurement adaptor 37 is recorded.

Stereo measurement to be performed by the measuring endoscope system 10 is achieved by activating at least first to sixth modules. Herein, the first module reads optical data from a recording medium (for example, a compact flash memory card) on which optical data concerning the stereo measurement adaptor 37 is recorded. The second module reads positional relationship data concerning the imaging device 43 included in the endoscopic distal part 39 and the stereo measurement adaptor 37. The third module calculates an error in the position of the imaging module included in the endoscope body from the positional relationship data read by the second module and positional relationship data between the endoscope and stereo measurement adaptor 37 that is detected in the course of manufacture. The fourth module corrects the optical data read from the recording medium according to the positional error calculated by the third module. The fifth module performs coordinate transformation on images to be measured according to the optical data corrected by the fourth module. The sixth module detects coordinates representing any point in the three-dimensional space by matching corresponding points rendered in the two images, which result from the coordinate transformation performed by the fifth module, with each other.

The CPU 26 activity, for example, the first to fourth modules once to the stero measurement adaptor 37, and extends control so that the results will be recorded as measuring environment data on the compact flash memory card 23. Hereinafter, when stereo measurement is performed, the CPU 26 loads the measuring environment data into the RAM, and activates the fifth and sixth modules.

In order to activate the second module, the CPU 26 detects the outline of a mask that is mounted on the optical adaptor and that is not shown, and compares the detected outline and position of the mask with those detected in the course of manufacture. In this case, the outline of the mask is detected by acquiring a white image (imaging a white sheet of paper or the like). The brightness of the white image is determined with a gain and a shutter speed which are determined by the CCU 25.

Normally, the CCU 25 is controlled so that the gain produced by the imaging device 43 and the shutter speed at which the imaging device 43 receives an optical image will be optimized automatically. However, when the outline of the mask mounted on the optical adaptor is imaged, the CCU 25 tends to decrease the gain but increase the shutter speed at which the imaging device 43 receives an optical image. Therefore, an image produced by the CCU 25 gets darker and the outline of the mask cannot be imaged distinctly. The image produced by the CCU 25 deteriorates the precision in stereo measurement.

According to the present embodiment, therefore, in the measuring endoscope system 10, the gain and shutter speed determined by the CCU 25 are fixed under the control of the CPU 26. Consequently, the measuring endoscope system 10 of the present embodiment can reliably image the outline of the mask mounted on the optical adaptor. The precision in measurement guaranteed by the measuring endoscope system 10 will not deteriorate.

Moreover, the measuring environment data includes a coordinate transformation table that contains an amount of data of, for example, 12M bytes. When three stereo measurement adaptors are registered, an amount of data required in relation to the adaptors comes to 36M bytes (=12M bytes×3).

The measuring environment data that is a large amount of data has been recorded on a recording medium such as a hard disk or a flash ROM incorporated in the system in the past.

However, the recording medium is unnecessary for users who do not need stereo measurement. Nevertheless, such users have to purchase an expensive measuring endoscope system that costs high because of inclusion of the recording medium.

In the measuring endoscope system 10 of the present embodiment, the CPU 26 extends control so that the environment data will be recorded on the compact flash memory card 23 that can be freely inserted or removed. Consequently, if a user who does not need stereo measurement selects a measuring endoscope system in which the compact flash memory card 23 is not inserted, the cost the user must incur can be decreased. In this case, when the user comes to need stereo measurement, the user should merely add the compact flash memory card 23 to his/her measuring endoscope system. Thus stereo measurement can be implemented easily.

Furthermore, in the measuring endoscope system 10 of the present embodiment, stored image data is recorded on the PCMCIA memory card 22 under the control of the CPU 26. Thus, the image data is recorded on a memory card other than the compact flash memory card 23 on which the measuring environment data is recorded.

Normally, when the storage capacity of the PCMCIA memory card 22 on which image data is recorded is used up, the PCMCIA memory card 22 is replaced with another. From this viewpoint, in the measuring endoscope system 10 of the present embodiment, measuring environment data and image data are recorded on different memory cards. This is advantageous in that a measuring environment can be managed easily.

The measuring endoscope system 10 of the present embodiment has been described to use the PCMCIA memory card 22 and compact flash memory card 23. Alternatively, for example, two PCMCIA memory cards 22 may be employed, and any other recording medium that can be freely inserted and removed (for example, a flexible disk) may be adopted. Nevertheless, the same advantages as those described above can be provided.

Next, the components of the normal optical adaptor employed in the measuring endoscope system 10 of the present embodiment will be described with reference to FIG. 6 to FIG. 8.

FIG. 6 and FIG. 7 show the endoscopic distal part 39 having the normal optical adaptor 42 attached thereto. The normal optical adaptor 42 is secured with the female screw 53 threaded on the locking ring 38 meshed with the male screw 54 threaded on the endoscopic distal part 39.

Moreover, the normal optical adaptor 42 has a pair of illumination lenses 41 and an objective lens 40 contained on the distal face thereof. The objective 40 converges an optical image on the imaging device 43 included in the endoscopic distal part 39. An image signal produced by the imaging device 43 is, similarly to that in the stereo measurement adaptor 37, propagated over the signal line 43a electrically coupled to the imaging device 43, and transmitted to the CCU 25 via the endoscope unit 24. The CCU 25 converts a received image signal into a video signal and transfers the video signal to the video signal processing circuit 33. Consequently, an image like the one shown in FIG. 8 is displayed on the LCD 14.

When the measuring endoscope system 10 of the present embodiment performs measurement using the normal optical adaptor, a comparison measurement technique is adopted. Specifically, comparison measurement to be performed in the present embodiment is a technique of performing measurement using a known dimension of a representation contained in an image displayed on the screen as a reference.

For example, when a user is aware of the dimension of a circle shown in FIG. 8, the user sets pointers at both ends of the diameter of the circle and enters a point-to-point length L1 45. A dimension L2 46 the user wants to learn is calculated based on the ratio thereof to L1 on the screen through an arithmetic operation performed by the CPU 26. At this time, the CPU 26 corrects a distortion of the image on the basis of the distortion characteristic of a lens employed so that the dimension can be calculated more accurately.

The distortion characteristic of a lens employed based on which a distortion is corrected is recorded in advance in the ROM 27. The CPU 26 loads data relevant to the selected normal optical adaptor 42 into the RAM 2 and carries out comparison measurement.

Next, control actions to be performed by the CPU 26 which feature the measuring endoscope system 10 of the present embodiment will be described with reference to FIG. 9.

Assume that the power supply of the measuring endoscope system 10 shown in FIG. 1 is turned on and the measuring endoscope system 10 is put to use. The CPU 26 runs a main program (see FIG. 9A), makes a judgment at steps S100, S101, S102, S103, and S109 respectively that constitute a loop, and enters a standby state. Moreover, when a specific facility is designated at step S100, S101, or S102, the CPU 26 passes control to a step at which the facility starts processing. If a facility is designated at step S103, control is passed to step S104.

At step S103, the CPU 26 judges whether any optical adaptor is designated as the one to be attached to the endoscopic distal part 39 or any optical adaptor is attached to the endoscopic distal part 39. If no optical adaptor is designated, the CPU 26 judges at step S109 whether the processing is terminated. If the CPU 26 judges that the processing is terminated, the CPU 26 completes the processing. Otherwise, control is returned to step S100.

On the other hand, if the CPU 26 judges at step S103 that an optical adaptor is attached to the endoscopic distal part 39 or an attached optical adaptor is designated, the CPU 26 passes control to step S104. By passing control to the judgment of step S104, the CPU 26 enters a wait state to wait until an action is made in order to call an optical adaptor designating facility.

For example, assume that a user attaches a certain optical adaptor to the distal endoscope part 39. The CPU 26 calls the optical adaptor designating facility and passes control to step S104. At step S104, the CPU 26 produces a display signal, which renders an optical adaptor selection screen image, on the basis of the designation performed by the optical adaptor designating facility that designates an attached optical adaptor. The CPU 26 transmits the produced display signal to the video signal processing circuit 33 (see FIG. 2), whereby the optical adaptor selection screen image like the one shown in FIG. 11 is displayed on the LCD 14.

The optical adaptor selection screen image is a screen image presenting, for example, the stereo measurement adaptor model AT60D/60D and the normal optical adaptor models AT120D and AT60D. A user designates an optical adaptor, which the user is currently using, by moving a cursor, which is not shown and displayed on the selection screen image, up and down using the lever switch 48.

Thereafter, the CPU 26 judges at step S105 whether the optical adaptor designated by the user is the normal optical adaptor.

If the designated optical adaptor is the normal optical adaptor, the CPU 26 sets a comparison measurement flag to 1 at step S106, and passes control to step S107. In contrast, if the designated optical adaptor is not the normal optical adaptor, the CPU 26 passes control to step S107.

At step S107, the CPU 26 judges whether the user-designated optical adaptor is the stereo measurement adaptor. If the designated optical adaptor is the stereo measurement adaptor, the CPU 26 sets a stereo measurement flag to 1 at step S108, and puts the measuring endoscope system 10 to a standby state until the user presses the measurement execution switch 51 of the remote controller 13. On the other hand, if the designated optical adaptor is not the stereo measurement adaptor, the CPU 26 puts the measuring endoscope system 10 to the standby state.

Thereafter, when the user presses the measurement execution switch 51 of the remote controller 13, the CPU 26 runs a routine described in FIG. 9B.

Specifically, the CPU 26 detects at step S110 whether the measurement execution switch (measurement execution key in FIG. 9B) 51 has been pressed, and judges at step S111 whether the stereo measurement flag is set to 1. At this time, if the CPU 26 judges at step S111 that the stereo measurement flag is set to 1, the CPU 26 judges that stereo measurement should be performed. At step S112, the CPU 26 executes stereo measurement described previously. When the stereo measurement is completed, the CPU 26 puts the system 10 to the standby state in preparations for display of the results of the measurement or re-measurement.

If it is judged at step S111 that the stereo measurement flag is not set to 1, the CPU 26 judges at step S113 whether the comparison measurement flag is set to 1. At this time, if it is judged at step S113 that the comparison measurement flag is set to 1, the CPU 26 judges that normal comparison measurement should be performed. At step S114, the CPU 26 executes the comparison measurement described previously. When the comparison measurement is completed, the CPU 26 puts the system 10 to the standby state for preparations of display of the results of the measurement or re-measurement.

If it is judged at step S113 that the comparison measurement flag is not set to 1, the CPU 26 returns control to step Sill or step S103 included in the main program described in FIG. 9A. Settings required for execution of measurement are checked again.

In the measuring endoscope system 10 of the present embodiment, when the measurement execution switch 51 of the remote controller is turned on, a measuring program whose activation is indicated with the flag is run. In other words, when the measurement execution switch 51 is pressed, a measuring technique associated with an attached optical adaptor is automatically implemented.

Moreover, in the measuring endoscope system 10 of the present embodiment, innovation has been made in order to improve the precision and efficiency in measurement. The measuring technique will be described with reference to FIG. 13 to FIG. 16.

A conventional measuring program includes steps of measuring a point-to-point length between points A and B in, for example, a point-to-point length measurement image shown in FIG. 13. However, when an object to be inspected has, as shown in FIG. 13, a curved crack 55 or any other damage on the surface thereof, the conventional measuring program measures as the length of the crack the length of a straight line linking the start and end points of the curve or repeatedly performs point-to-point length measurement along the curve. The efficiency in measurement performed by the conventional measuring program is thus poor.

The measuring endoscope system 10 of the present embodiment includes a measuring means that when three or more points, for example, points A, B, C, and D are designated on the screen as shown in FIG. 14, measures a sum total of lengths of segments, that is, a segment starting at point A and subsequent segments.

Consequently, the measuring endoscope system 10 of the present embodiment has succeeded in further improving the efficiency in inspection. This type of measuring means is adapted to stereo measurement or comparison measurement.

For a measuring technique, it is essential not only to measure the length of an object to be inspected but also to measure the area thereof.

The conventional measuring, program includes not only the steps of measuring a point-to-point length as mentioned above but also the steps of measuring a depth from the surface of an object to be inspected. However, the conventional measuring program cannot measure the area of a corroded portion of the surface of an object to be inspected.

According to the present embodiment, the measuring endoscope system 10 includes a measuring means that: when a plurality of points, for example, points A to G are, as shown in FIG. 15, designated on the screen, successively traces the points to draw segments; and that when a graphic defined with the segments is closed, calculates the area of the graphic.

Talking of an actual procedure, a user designates a plurality of points A to G as shown in FIG. 15. The CPU 26 sequentially traces the plurality of points to draw segments. When a graphic defined with the segments is closed, point H is designated so that the segment ending at point H will intersect the first segment AB.

Accordingly, the measuring program recognizes a point closest to point H shown in FIG. 15 as a final point (point A in FIG. 16) as shown in FIG. 16 so as to close the graphic defined with the segments. Thereafter, the measuring program divides the closed graphic into a plurality of triangles, and calculates a sum total of the areas of the triangles. This kind of measuring means is adapted to both stereo measurement and comparison measurement.

In the measuring endoscope system 10 of the present embodiment, when the foregoing measuring technique is adopted, the precision and efficiency in measurement can be improved.

According to the present embodiment, when a user attaches an optical adaptor to the endoscopic distal part of the measuring endoscope system 10, the user designates the model of the optical adaptor. Thereafter, the user should merely press the measurement execution switch. Thus, a measuring program optimal to the attached optical adaptor is automatically and immediately run.

Therefore, the measuring endoscope system 10 of the present embodiment can perform measurement more efficiently than the conventional one can. Moreover, handling needed to instruct the measurement is simple. Consequently, the measuring endoscope system 10 of the present embodiment wipes out the fear that a measuring technique unassociated with an optical adaptor may be implemented, and can accurately and correctly measure an object to be inspected.

(Second Embodiment)

According to the present embodiment, in efforts to more quickly implement an optimal measuring technique, a program to be run in the measuring endoscope system 10 of the first embodiment has been innovated. The second embodiment is different from the first embodiment in terms of this point.

To be more specific, in the measuring endoscope system of the second embodiment, a measuring technique is implemented by selecting a menu item from a menu presented by a measuring program under the control of the CPU 26 but not by pressing the measurement execution switch 51.

In the measuring endoscope system of the second embodiment, a program to be run by the CPU 26 is almost identical to the one described in the flowchart of FIG. 9A and installed in the first embodiment except that the measurement execution routine (except step S110) described in FIG. 9B is run as facility 1 to be activated at step S100.

The other features are substantially identical to those of the measuring endoscope system 10 of the first embodiment.

The measuring endoscope system of the second embodiment acts substantially in the same manner as the measuring endoscope system 10 of the first embodiment. However, after the power supply of the system is turned on, when an attempt is made to perform measurement, the CPU 26 acts as described below.

The instant the power supply of the system is turned on, the CPU 26 makes a judgment at step S111 included in the routine described in FIG. 9B. Thereafter, similarly to the CPU included in the first embodiment, the CPU 26 extends control so that stereo measurement or comparison measurement will be carried out. The other operations are identical to those of the first embodiment.

According to the second embodiment, the measuring endoscope system can provide the same advantages as the first embodiment does. Furthermore, a procedure needed to instruct measurement is simplified, and the measurement is carried out immediately.

According to the present invention, it is apparent that a wide range of different embodiments can be formed based on the invention without a departure from the spirit and scope of the invention. The present invention will be limited by the appended claims but not restricted by any specific embodiment.

What is claimed is:

1. A measuring endoscope system for processing object image data produced by imaging an object to be inspected and measuring the object to be inspected, comprising:
    a plurality of types of optical adaptors each freely detachably attached to an endoscopic distal part in order to converge an object image on an imaging device included in said endoscopic distal part, said plurality of types of optical adaptors including a first type of optical adaptor having one objective lens and a second type of optical adaptor having two objective lenses;
    a menu display module for selecting a selection menu according to display data associated in advance with each of said plurality of optical adaptors; and
    a measuring means for performing measurement according to the result of the selection performed by said menu display module.

2. A measuring endoscope system according to claim 1, wherein said plurality of types of optical adaptors includes two types of optical adaptors, that is, a stereo measurement adaptor needed to perform stereo measurement and a normal measurement adaptor needed to perform normal comparison measurement.

3. A measuring endoscope system according to claim 2, wherein said measuring means comprises:
    a first module for reading optical data from a recording medium on which optical data concerning said stereo measuring adaptor is recorded;
    a second module for reading positional relationship data between said imaging device included in said endoscopic distal part and said stereo measurement adaptor;
    a third module for calculating an error in the position of said imaging device included in said endoscopic distal part on the basis of the positional relationship data read by said second module and positional relationship data between an endoscope and said stereo measurement adaptor which is key data acquired in the course of manufacture;
    a fourth module for correcting the optical data read from the recording medium according to the positional error calculated by said third module;
    a fifth module for performing coordinate transformation on images to be measured according to the optical data corrected by said fourth module; and
    a sixth module for detecting coordinates, which represent any point in the three-dimensional space, by matching corresponding points in the two images, which result from the coordinate transformation performed by said fifth module, with each other.

4. A measuring endoscope system according to claim 3, wherein: said measuring means detects the outline of a mask mounted on said optical adaptor, compares the outline and position of the mask with the outline and position thereof detected in the course of manufacture; and when said second module is activated, said measuring means sets a gain produced by said imaging device and a shutter speed, at which said imaging device receives an optical image, to certain values.

5. A measuring endoscope system according to claim 3, wherein said measuring means activates said first to fourth modules relative to said stereo measurement adaptor, and records the results as measuring environment data.

6. A measuring endoscope system according to claim 5, wherein said measuring means records the measuring environment data and endoscopic image data on different recording media.

7. A measuring endoscope system according to claim 6, wherein the recording medium on which the measuring environment data is recorded is a compact flash memory card that can be freely inserted or removed.

8. A measuring endoscope system according to claim 2, wherein said stereo measurement adaptor has two objectives contained in the distal face thereof, and the two objectives converge two images on said imaging device incorporated in said endoscopic distal part.

9. A measuring endoscope system according to claim 1, wherein said measuring means performs measurement automatically upon activation by a user of the measuring means.

10. A measuring endoscope system according to claim 1, further comprising a video signal processing circuit for displaying an endoscopic image picked up by said imaging device or a produced selection menu, wherein:
    said menu display module selects a selection menu to be presented on an image displayed by said video signal processing circuit.

11. A measuring endoscope system according to claim 10, wherein said video signal processing circuit synthesizes the endoscopic image and the selection menu to produce a synthetic image.

12. A measuring endoscope system according to claim 1, further comprising a remote controller to be handled in order to control various actions that are performed in the entire system, wherein:
    said menu display module selects a selection menu according to an instruction given by handling said remote controller.

13. A measuring endoscope system according to claim 12, wherein said remote controller has: a joystick used to angle said endoscopic distal part; a lever switch used to move a pointer for the purpose of selecting a menu item from various menus displayed on a screen or performing measurement; a Freeze switch used to display an image frame included in an endoscopic motion picture as a still image; a Store switch that when a still image is displayed by pressing said Freeze switch, is used to record the still image data on a recording medium; and a measurement execution switch used to run measuring software.

14. A measuring endoscope system according to claim 13, wherein said measuring software judges whether an optical adaptor to be attached to said endoscopic distal part has been designated, or judges whether an optical adaptor has been attached and whether the optical adaptor has been designated, and performs measurement.

15. A measuring endoscope system for processing object image data produced by imaging an object to be inspected and measuring the object to be inspected, comprising:
    a plurality of types of optical adaptors each freely detachably attached to an endoscopic distal part in order to converge an object image on an imaging device included in said endoscopic distal part;

a menu display module for selecting a selection menu according to display data associated in advance with each of said plurality of optical adaptors; and a measuring means for performing measurement according to the result of the selection performed by said menu display module, wherein said plurality of types of optical adaptors include two types of optical adaptors, that is, a stereo measurement adaptor to perform stereo measurement and a normal measurement adaptor to perform normal comparison measurement, and wherein when said measuring means performs stereo measurement or comparison measurement, said measuring means prompts a user to designate at least three or more points in an endoscopic image displayed on a screen, and calculates the sum total of the lengths of segments drawn by tracing the points.

16. A measuring endoscope system for processing object image data produced by imaging an object to be inspected and measuring the object to be inspected, comprising:

a plurality of types of optical adaptors each freely detachably attached to an endoscopic distal part in order to converge an object image on an imaging device included in said endoscopic distal part;

a menu display module for selecting a selection menu according to display data associated in advance with each of said plurality of optical adaptors; and a measuring means for performing measurement according to the result of the selection performed by said menu display module, wherein said plurality of types of optical adaptors include two types of optical adaptors, that is, a stereo measurement adaptor to perform stereo measurement and a normal measurement adaptor to perform normal comparison measurement, and wherein when said measuring means performs stereo measurement or comparison measurement, said measuring means prompts a user to designate a plurality of points in an endoscopic image displayed on a screen, successively traces the points to draw segments, calculates the area of each of the divisions of a graphic defined with the segments, and measures the overall area of the graphic by summing up the areas of the divisions.

* * * * *